United States Patent [19]

Hayashi et al.

[11] Patent Number: 4,891,168

[45] Date of Patent: Jan. 2, 1990

[54] PROCESS FOR PRODUCING STEROID DERIVATIVES

[75] Inventors: Sei-ichi Hayashi; Tadashi Hohjoh, both of Ageo; Tokuo Furuse, Iseharaa; Hiroki Kuriyama, Naka; Tsuyoshi Watanabe, Isehara; Suguru Takatsuto, Joetsu, all of Japan

[73] Assignees: Nippon Kayaku Kabushiki Kaisha; Tama Biochemical Co., Ltd., both of Tokyo, Japan

[21] Appl. No.: 96,433

[22] Filed: Sep. 15, 1987

[30] Foreign Application Priority Data

Sep. 25, 1986 [JP] Japan ................................. 61-224843
Oct. 21, 1986 [JP] Japan ................................. 61-248408
Oct. 21, 1986 [JP] Japan ................................. 61-248409

[51] Int. Cl.$^4$ ................................................ C07J 9/00
[52] U.S. Cl. ............................. 260/397.2; 260/397.25
[58] Field of Search ........................... 71/88; 549/268; 260/397.25, 397.2

[56] References Cited

FOREIGN PATENT DOCUMENTS 040517 11/1981 European Pat. Off. ............ 549/268
60-139685 7/1985 Japan .

OTHER PUBLICATIONS

A New Synthesis of Brassino Steroids: Plant Growth Promoting Steroids, Anastasia et al., J. Chem. Soc. (PKI), 1983, pp. 379-381.
Reagents for Organic Chemistry, Fieser et al., (1967), pp. 142-147.
Some Modern Methods in Organic Synthesis (2nd Ed.), Carruthers, (1978), pp. 338-343.
Synthesis and Biological Activity of Brassinolide and its 22B,22B Isomer: Novel Plant-Growth-Promoting Steroids, Thompson et al., Steroids, (1981), vol. 38, pp. 567-579.
John Fried and John A. Edwards, Organic Reactions in Steroid Chemistry, vol. 1, pp. 232-233, (1972).
N. F. Blau and C. G. Stuckwisch, The Reaction of Dimethyl Sulfide with 3,5-Cyclosteroids, J. Org. Chem., 27 (2), p. 370, (1962).
Harold R. Nace, The Reaction of α- and β-cholestanyl p-toluenesulfonates with Methanol, JACS, vol. 74, p. 5937, (1952).
Steroids, vol. 45, No. 6, Jun. 1985, pp. 561-564.
Chemical Pharmaceutical Bulletin, vol. 32, No. 5, May 1984, pp. 2001-2004.
Chemical Abstracts, vol. 105, No. 17, Oct. 27, 1986, pp. 726-727, Abstract No. 153400s.

Primary Examiner—H. M. S. Sneed
Assistant Examiner—J. Saba
Attorney, Agent, or Firm—Nixon & Vanderhye

[57] ABSTRACT

A process for producing a steroid compound which is useful as an intermediate for synthesizing plant growth regulators, brassinosteroids, and is represented by the general formula (4):

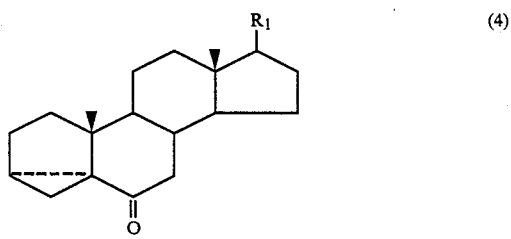

(4)

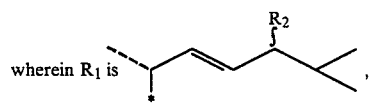

in which $R_2$ is a methyl or ethyl, and * indicates the binding site of $R_1$ to a steroid nucleus, or general formula (5):

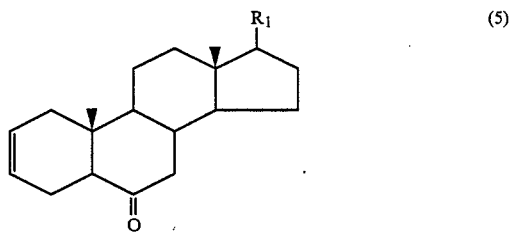

(5)

wherein $R_1$ is as defined above.

According to the process disclosed herein, an intermediate for a brassinolide, epibrassinolide, homobrassinolide or derivatives thereof can be produced highly advantageously in the industries.

7 Claims, No Drawings

PROCESS FOR PRODUCING STEROID DERIVATIVES

DETAILED DESCRIPTION OF THE INVENTION

The present invention relates to a process for producing a steroid compound, which is useful as an intermediate for synthesizing plant growth regulators, brassinosteroids, or in more detail, relates to a process for producing a steroid compound represented by the general formula:

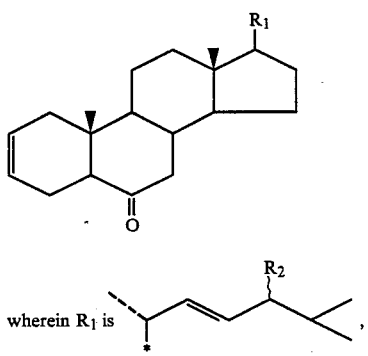

wherein $R_1$ is

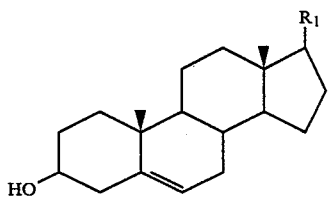

wherein $R_1$ is in which $R_2$ is a methyl or ethyl, and * indicates the binding site of $R_1$ to a steroid nucleus, which comprises reacting a compound represented by the formula:

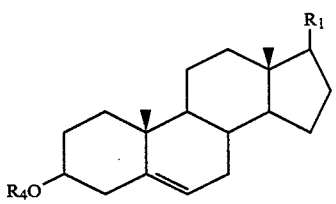

wherein $R_1$ is as defined above, with $R_3SO_2X$, wherein $R_3$ is a lower alkyl, preferably $C_1-C_4$ alkyl, or a phenyl which may be substituted by methyl or chlorine atom, and X is a chlorine or fluorine atom, in the presence of an organic base in solvents such as an aromatic or aliphatic hydrocarbon to produce a compound represented by the formula:

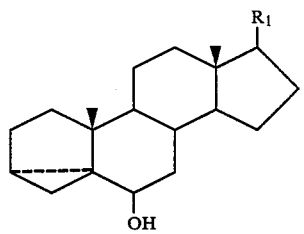

wherein
  $R_4$ is $R_3SO_2-$, and
  $R_1$ and $R_3$ are as defined above, then reacting the above compound with water in the presence of an inorganic or organic base in a mixture of an aromatic or aliphatic hydrocarbon and an inert and water miscible organic solvent to produce a compound represented by the formula:

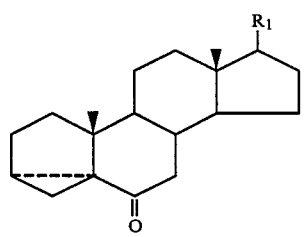

wherein $R_1$ is as defined above, and subsequently oxidizing the above compound, (1) in the presence of a ketone compound in an aromatic or aliphatic hydrocarbon or (2) in the presence of a quaternary ammonium halide in an appropriate solvent by means of an N-halocarboxamide to produce a steroid compound represented by the formula:

wherein $R_1$ is as defined above, and finally heating the above compound in the presence of an amine salt of an organic or inorganic sulfonic acid or a compound having both sulfo group and amino group in a molecule, in an organic solvent.

Processes for producing the intended steroid compound represented by the formula (4) from the compound represented by the formula (1) as a starting material are known as described in J. Org. Chem., 28, 571 (1963), J. Am. Chem. Soc., 62, 3346–3348(1940) and Japanese Patent Publication No. 17794/1985. In addition, to obtain a compound of the formula (5) from a compound of the formula (4), the method is described in Steroids, 38, 5 (1981), J. Chem. Soc. P.T.I. 1983, 379, Japanese Patent Laid-Open No. 69790/1986 and No. 161384/1981 are known.

However, all the three processes for producing the compound of the formula (4) from the compound of the formula (1) by the above literatures need operations to wash with water and remove the reaction solvent, and then to distill off the solvent in every process, and so are not advantageous industrially.

Besides, the above four processes for producing the compound of the formula (5) from the compound of the formula (4), for example, give a low yield, or need to react in an atmosphere such as argon and nitrogen, so they are not advantageous industrially.

Therefore, the inventors of the present invention have investigated intensively to improve the process for producing the compound of the formula (4) or (5) and its derivatives so as to be easily operated industrially.

The inventors of the present invention have investigated the reaction conditions of each reaction process by using a compound represented by the formula:

wherein $R_1$ is

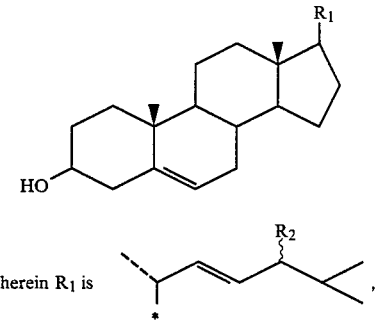

wherein $R_2$ is a methyl, or ethyl, and * indicates $R_1$'s binding site to a steroid nucleus,
as a starting material, and as a result they have found a process for producing the intended compound represented by the formula:

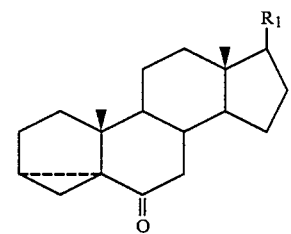

or

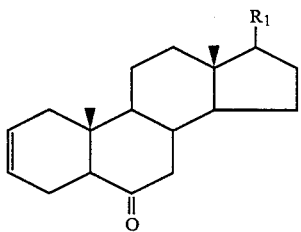

by easy operations of each processes in a favorable yield. The present invention will be illustrated in detail below.

First, a compound represented by the formula

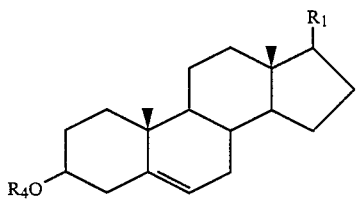

wherein
$R_4$ is $R_3SO_2$-, and
$R_1$ and $R_3$ are as defined above,
can be obtained by reacting a compound of the formula (1) with $R_3SO_2X$ wherein $R_3$ and $X$ are as defined above, in solvents such as an aromatic or aliphatic solvent, in the presence of an organic base. In this reaction, as examples of the aromatic or aliphatic solvent, there may be benzene, toluene, xylene, n-hexane, n-heptane, cyclohexane and methylcyclohexane, and 5 to 20 parts of these compounds are preferably used to 1 part of a compound of the formula (1) in terms of weight.

As examples of the base, there may be mentioned pyridine, picoline, triethylamine and trimethylamine, and 1.0 to 5.0 mol of these bases are preferably used to 1 mol of a compound of the formula (1).

As examples of $R_3SO_2X$, there may be mentioned methanesulfonyl chloride, methanesulfonyl fluoride, p-chlorobenzenesulfonyl chloride, p-toluenesulfonyl chloride and p-toluenesulfonyl fluoride and 1.0 to 2.0 mol of these compounds are preferably used to 1 mol of a compound of the formula (1).

Further, a reaction temperature is preferably below room temperature and the reaction generally completes in 0.5 to 2 hours.

A compound represented by the formula:

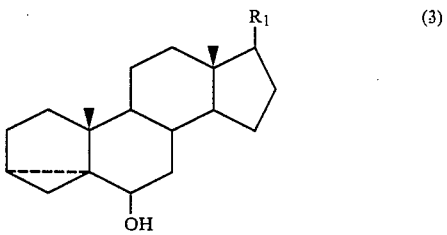

wherein $R_1$ is as defined above, can be obtained by isomerizing a compound of the formula (2). In this reaction, the same solvent can be used also as the aromatic or aliphatic hydrocarbon solvents used to obtain the compound (2) from the above compound (1). Namely, a compound (3) can be produced by reacting a compound of the formula (2) with water in the presence of an inorganic or organic base, and if necessary, further in the presence of a phase transfer catalyst, in a solvent mixture of an aromatic or aliphatic hydrocarbon and an inert water-miscible organic solvent.

In this reaction, as examples of the inorganic or organic base, there may be mentioned alkali hydroxides such as KOH and NaOH, alkali carbonates or bicarbonates such as $Na_2CO_3$, $NaHCO_3$, $K_2CO_3$ and $KHCO_3$, alkali-metal salts of an organic acid such as $CH_3COON$ and $CH_3COOK$, and tertiary amines such as pyridine, picoline and triethylamine, and preferably $Na_2CO_3$ and $K_2CO_3$ can be used. 1.0 to 2.0 mol of these inorganic or organic bases are preferably used to 1 mol of a compound of the formula (2).

As examples of the phase transfer catalyst, there may be mentioned quaternary ammonium salts such as tetra-n-butylammonium bromide, tetra-n-butylammonium chloride, benzyltriethylammonium chloride, benzyltriethylammonium bromide, benzyltrimethylammonium chloride, and methyl tri-2-methylphenylammonium chloride, phosphonium compounds such as tetramethylphosphonium iodide and tetra-n-butylphosphonium bromide, and sulfate compounds such as methyldinonylsulfonium methylsulfate and benzyltriethylammonium sulfate, and 0.02 to 0.2 parts of the compounds are preferably used to 1 part of a compound of the formula (2) in terms of weight.

Next, as examples of the inert water-miscible solvent, there may be mentioned ketones such as acetone, methylethylketone, diethylketone and methylisopropylketone, cyclic ethers such as dioxane, and tetrahydrofuran, and amides such as dimethylformamide and dimethylacetamide. A mixing ratio of these solvents to water is preferably to the extent from 1:0.05 to 1:0.3.

As examples of the solvent such as an aromatic or aliphatic hydrocarbon, there may be mentioned the ones described in the production of the above compound (2). A mixing ratio of these solvents and a water-miscible solvent is preferably to the extent from 1:0.5 to 1:5. Further, the reaction temperature is preferably at from room temperature to near the boiling point of the solvent mixture.

A compound represented by the formula

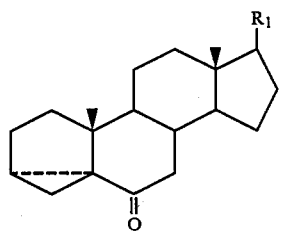

wherein $R_1$ is as defined above, can be obtained by oxidizing a compound of the formula (3). As a reaction solvent for this oxidation reaction, the same solvent such as aromatic or aliphatic hydrocarbons used for producing the compound (2) from the compound (1), or the compound (3) from the compound (2) can be used as it is.

As examples of the oxidation reaction using ketone, there may be mentioned Jones oxidation, known by J. Chem. Soc., 1946, 39 (a method using a dilute sulfuric acid solution of chromium (VI) oxide in ketone) and Oppenauer oxidation described in "Oxidation and Reduction, I-2" pp. 803 to 828 in the Shin Jikkenkagaku Koza 15 (published by Maruzen K.K., Sept. 20, 1976) (a method using a carbonyl compound and aluminium alkoxide).

As examples of the ketones to be used in this oxidation, there may be mentioned acetone, methyl ethyl ketone, diethyl ketone, methyl isobutyl ketone, cyclohexanone and benzoquinone.

An optional proportion of the ketone may be added to a compound of the formula (3); preferably 1.0 to 10 parts in Jones oxidation and 3 to 200 equivalents in Oppenauer oxidation. A mixing ratio of solvents such as an aromatic or aliphatic hydrocarbon and ketones may be selected to an appropriate extent, preferably in a range 0.1 to 2 parts by weight.

In addition, a product formed by the above reaction operations is traced by means of thin-layer chromatography in course of reaction, and after the reaction finished, the intended product can be obtained by the general procedure of treatment, that is, dilution by water, extraction by an organic solvent and recovery, washing with an acid or alkali, and washing the extract with water to neutral, subsequent drying over magnesium sulfate, filtration and removal of solvent by vacuum evaporation, and if necessary, by purification by means of silica-gel column chromatography.

Another method for producing the compound of the formula (4) is that the compound of the formula (4) can be obtained by oxidizing a compound of the formula (3) with an N-halocarboxamide in the presence of a quaternary ammonium halide in an appropriate solvent.

This process ( (3)→(4) ) has no necessity of using Jones Reagent that toxic chromium (VI) is used and any compound with a protecting group can not be used because the reaction is carried out in a strong acid.

In this reaction, as examples of the quaternary ammonium halide, there may be mentioned tetra-n-butylammonium chloride, tetra-n-butylammonium bromide, tetra-n-butylammonium iodide, benzyltriethylammonium chloride, benzyltriethylammonium bromide, benzyltriethylammonium iodide, benzyltrimethylammonium chloride, benzyltrimethylammonium bromide and benzyltrimethylammonium iodide, and among them is more preferrably tetra-n-butylammonium iodide. 1.0 to 5.0 mol of these salts are preferably used to 1 mol of a compound of the formula (3).

As examples of the N-halocarboxamide used as an oxidizing agent, N-bromosuccinimide, N-iodosuccinimide, N-bromophthalimide, N-iodophthalimide, N-bromoacetamide, N-iodoacetamide, N-bromocaprolactam and N-iodocaprolactam are mentioned, and 2 to 10 mol of these compounds are preferably used to 1 mol of a compound of the formula (3).

As examples of the appropriate solvent, halogenated hydrocarbons such as methylene chloride, chloroform, carbon tetrachloride, 1,2-dichloroethane, 1,1,1-trichloroethane, trichloroethylene, tetrachloroethylene, monochlorobenzene and dichlorobenzene, aromatic or aliphatic hydrocarbons such as n-hexane, benzene, toluene and xylene, and ethers such as ethyl ether and dioxane are mentioned. A reaction temperature is preferably at a room temperature or near the boiling point of a solvent.

Furthermore, a compound of the formula (5) may be produced from a compound of the formula (4) by the following procedure.

The intended compound represented by the formula (5) can be obtained by heating a compound of the formula (4) in the presence of an amine salt of an organic or inorganic sulfonic acid, or a compound having both a sulfo group and an amino group in the same molecule, in an organic solvent.

In this reaction, as examples of the organic or inorganic sulfonic acid, sulfonic acid, p-toluenesulfonic acid, p-chlorobenzenesulfonic acid, 10-camphorsulfonic acid, benzenesulfonic acid, m-xylene-4-sulfonic acid and naphthalene-$\beta$-sulfonic acid are mentioned, and for example of an amine, ethylamine, diethylamine, morpholine, piperidine, triethylamine, pyridine, picoline, benzyltriethylamine, ammonia, cyclohexylamine, t-butylamine, diphenylamine, aniline and n-propylamine. As examples of the compound having both a sulfonic acid and an amino group in a molecule, sulfamic acid, sulfanilic acid, phenylsulfanilic acid, taurine, naphthionic acid and cyclamic acid.

Thereupon, an amine salt of a sulfonic acid may be any combination between the above sulfonic acids and amines, and for example of more preferable combination, pyridinesulfate, pyridine-p-toluenesulfonate, triethylamine-sulfate, triethylamine-p-toluenesulfonate and pyridine-10-camphorsulfonate. As examples of a compound having both a sulfo group and an amino group in the same molecule, sulfamic acid and sulfanilic acid are preferably mentioned. An optional amount of these compounds maybe used to 1 mol of a compound of the formula (4), preferably 0.1 to 5.0 mol of them.

As examples of the reaction solvent, there may be mentioned common organic solvents such as hydrocarbon solvents including n-heptane, cyclohexane, methylcyclohexane, benzene, toluene, xylene, ethylbenzene and diethylbenzene, or aprotic polar solvents such as dimethylformamide, dimethylacetamide, N-methylpyrrolidone, dimethylsulfoxide and sulfolane, and they may be used either alone or as a solvent mixture. A reaction temperature is a boiling point of a solvent, or above 100° C., preferably 150 to 200° C.

In addition, a product formed by the above reaction operations is traced by means of thin-layer chromatography in course of reaction, and after the reaction finished, the intended product can be obtained by the general procedure of treatment, that is, dilution with water, extraction by an organic solvent, washing with an acid and alkali, and washing the extract with water to neutral, subsequent drying over magnesium sulfate, filtration and removal of solvent by vacuum evaporation, and, if necessary, by purification by means of silica-gel column chromatography.

According to the present invention, the compound of the formula (4) or (5) can be obtained from the compound of the formula (1) as a starting material in high yield and economically. That is, it is possible to conduct sequential three or four reactions for preparing the compound of the formula (4) or (5) in one reaction vessel using the same aromatic or aliphatic hydrocarbon as the solvent, adding a reagent, catalyst or other solvent for each reaction.

The present invention will be illustrated by the following Examples.

EXAMPLE 1: Synthesis of (22E,24R)-3α,5-cyclo-5α-ergost-22-en-6-one 42 ml of toluene and 8.7 ml (62.70 mmol) of triethylamine were added to 5.0 g (12.54 mmol) of brassicasterol and cooled. Under stirring the mixture, 2.0 ml (25.08 mmol) of mesyl chloride were gradually added dropwise thereto. After the reaction finished, the reaction product was washed by brine, 1N-hydrochloric acid and an aqueous sodium bicarbonate respectively in this sequence. Then, 126 ml of acetone, 25 ml of water and 1.29 g (12.17 mmol) of sodium carbonate were added thereto, and reacted by heating under reflux for about 12 hours. After the completion of the reaction was confirmed by means of thin-layer chromatography, acetone was distilled off and the residue was left to cool. The organic layer was separated by adding 58 ml of toluene and brine. The obtained organic layer was cooled and 10 ml of acetone were added thereto. 5.7 ml (CrO$_3$ 1.1 g contained) of Jones reagent were added while keeping below 0° C., and further stirred for 2 hours. After the reaction finished, methanol was added thereto and stirring was continued. After that, the organic layer was separated by adding brine, then washed with an aqueous sodium bicarbonate and by brine, respectively. The extract was dried over magnesium sulfate, and then concentrated and dried up to give a crude cyclo-6-one compound. The crude product was purified by means of a silica-gel column chromatography (hexane/ethyl ether =15/1) to 4.12 g (82.8 %) of the intended (22E, 24R)-3α,5-cyclo-5α-ergost-22-en-6-one.

m.p. 107°-109° C. (m.p. 108°-110° C. by literature[1]))
IR: 1705 cm$^{-1}$ ($\nu_{c=o}$)
$^1$Hnmr (CDCl$_3$)δ5.2 (2H, m, 22- and 23-H)
Literature[1]) M. Anastassia., P. Ciuffreds, and A. Fiecchi, J. Chem. Soc. P.T.I. 1983, 379

Example 2: Synthesis of stigmasteryl mesylate 25.0 g (60.6 mmol) of stigmasterol, 200 ml of toluene and 42.1 ml of triethylamine are mixed together and cooled. While stirring the mixture 9.4 ml (0.12 mol) of mesyl chloride were gradually added dropwise thereto. After the reaction finished, triethylamine hydrochloride was filtered off, and the filtrate was washed by brine, 1N-aqueous hydrochloric acid and aqueous sodium bicarbonate in this sequence. The filtrate was dried over magnesium sulfate, then concentrated and evaporated to dryness to give 29.1 g (97.8 %) of the mesylate.

Example 3: Synthesis of brassicasteryl tosylate 65 g (16.3 mmol) of brassicasterol, 52 ml of benzene and 6.6 ml of pyridine were mixed together and cooled. While stirring the mixture, 6.2 g (32.6 mmol) of p-toluenesulfonyl chloride were added gradually. After the reaction was finished, the product was washed by brine, 1N-hydrochloric acid and aqueous sodium bicarbonate, dried over magnesium sulfate, and then concentrated and evaporated to dryness to give 8.8 g (97.7%) of the tosylate.

EXAMPLE 4: Synthesis of 24S-ethyl-3α,5-cyclo-5α-cholest-22E-en-6β-ol(i-stigmasterol)

590 mg (1.20 mmol) of the above mesylate obtained in Example 2 were dissolved in 3.7 ml of toluene and 11 ml of acetone and heated under reflux. A solution of 130 mg (1.23 mmol) of sodium carbonate in 2.2 ml of water was added thereto and continuously heated further for 11 hours. After the reaction finished, the mixture was left to cool room temperature. The organic layer was separated by adding 10 ml of toluene and brine, and the extract was dried over magnesium sulfate, then concentrated and dried up. The product was purified by means of silica-gel column chromatography to 413 mg (83.3%) of the i-stigmasterol.

m.p. 49° to 51° C. (50° to 52° C. by literature[2])
$^1$H nmr (CDCl$_3$): δ3.13 (1H, b) 5.08 (2H, m, 22- and 23H) Literature[2]: K. Mori et al., Tetrahedron, 38, 2099 (1982)

EXAMPLE 5: Synthesis of i-stigmasterol 510 mg (1.04 mmol) of the above mesylate obtained in Example 2, were dissolved in 6 ml of toluene, and in a separate vessel, 9 ml of acetone, 3 ml of water and 144 mg (1.04 mmol) of potassium carbonate were mixed together and heated under reflux. To the latter mixture, the toluene solution was gradually added dropwise, and reflux was further continued. After the reaction was finished, the similar operations and purification to Example 4 were operated to give 364 mg (84.8%) of the i-stigmasterol.

EXAMPLE 6: Synthesis of (22E, 24R)-3α,5-cyclo-5α-ergost-22-en-6β-ol(i-brassicasterol)

663 mg (1.20 mmol) of the above tosylate obtained in Example 3, were dissolved in 6 ml of benzene and 6 ml of dimethylformamide and heated under reflux. 200 mg (2.40 mmol) of sodium hydrogen carbonate dissolved in 3 ml of water, were added thereto, and reflux was continued for 3 hours. It was followed by the similar operations and purification to Example 2 to give 354 mg (74.0%) of the i-sterol.

m.p. 111° to 113° C. (m.p. 113° to 115° C. by literature[3])
$^1$H nmr (CDCl$_3$): δ0.3 to 0.5 (3H, m,) 5.1 (2H, m, 22- and 23H)
Literature[3]: M. J. Thompson, C. F. Cohen, S. M. Lancaster, Steroids, 7, 745 (1965)

EXAMPLE 7: Synthesis of i-brassicasterol 6 ml of dioxane, 3 ml of water and 220 mg (2.08 mmol) of sodium carbonate were mixed together and heated under reflux. A solution of 564 mg (1.02 mmol) of the above tosylate obtained in Example 3 in 6 ml of benzene were gradually added dropwise thereto and reacted further for 9 hours. After the reaction finished, it was followed by the similar operations and purification to Example 2 to give 298 mg (73.7 %) of the i-sterol.

Example 8: Synthesis of i-brassicasterol 3.7 g (35 mmol) of sodium carbonate were dissolved in 100 ml of water, and a solution of 17.7 g (32 mmol) of the above tosylate obtained in Example 3 in 750 ml of toluene/acetone (9:1) were added thereto. 1.0 g (3.1 mmol) of tetra-n-butylammonium bromide were added also, and reacted at 70° C. for 12 hours. The toluene layer was separated, and subjected to the similar operations and purification to Example 2 to give 10.4 g (81.7 %) of the i-brassicasterol.

Example 9: Synthesis of 24S-ethyl-3α,5-cyclo-5α-cholest 22E-en-6-one 300 mg (0.727 mmol) of i-stigmasterol were dissolved in 7 ml of toluene and 3 ml of acetone and cooled to 0° C. 0.6 ml ($CrO_3$ 0.12 g contained) of Jones reagent were added dropwise thereto so gradually that the reaction temperature does not exceed 0° C., then the reaction finished by stirring at 0° C. for 1 hour. Methanol was added thereto and stirred for a while, then the organic layer was separated by adding 10 ml of toluene and water. After washing with brine, aqueous sodium bicarbonate and brine succesively, the extract was dried over magnesium sulfate, and concentrated to give 293 mg (98.1 %) of the intended ketone compound. m.p. 98° to 100° C. (98 to 99° C. by literature[2]))
IR: 1685 cm$^{-1}$ ($\nu_{c=o}$)
$^1$H nmr (CDCl$_3$) : δ5.15 (2H,m 22- and 23-H)

Example 10: Synthesis of (22E, 24R)-3α,5-cyclo-5α-ergost-22-en-6-one 500 mg (1.25 mmol) of i-brassicasterol were dissolved in 10 ml of toluene and 1 ml of acetone and cooled to 0° C., 1.0 ml ($CrO_3$ 0.2 g contained) of Jones reagent were added thereto. It was followed by the procedure similar to Example 9 to give 480 mg (96.8 %) of the intended ketone compound.

Example 11: Synthesis of (22E, 24R)-3α,5-cyclo-5α-ergost-22-en-6-one 500 mg (1.25 mmol) of i-brassicasterol, 1.24 g (12.6 mmol) of cyclohexanone and 3 ml of toluene were mixed together and heated. A solution of 0.256 g (1.25 mmol) of aluminium isopropoxide in 5 ml of toluene was gradually added dropwise also thereto. After the addition was finished, reflux was continued for about 1 hour. After the reaction finished, the mixture was cooled and 10 ml of 10 % aqueous solution of sulfuric acid were added thereto. After stirred well, the toluene layer was washed by water and dried over magnesium sulfate, followed by distilling toluene off to give a crude product. The crude product was purified by means of silica-gel column chromatography (hexane/ether=15/1) to 372 mg (75.0 %) of the intended compound.

Example 12: Synthesis of (24E, 24R)-3α,5-cyclo-5α-ergost-22-en-6-one 1.13 g (5 mmol) of N-iodosuccinimide and 0.37 g (1 mmol) of tetra-n-butylammonium iodide were dissolved in 10 ml of methylene chloride, and a solution of 0.40 g (1 mmol) of i-brassicasterol in 3 ml of methylene chloride were added dropwise thereto. After reacting at room temperature for 10 hours, or at 40° C. for 3 hours, 20 ml of a saturated aqueous solution of sodium thiosulfate were added thereto. The methylene chloride layer was separated and washed by brine, followed by drying over sodium sulfate. After distilling off the solvents under a reduced pressure, the crude product was purified by means of silica-gel column chromatography (eluted by n-hexane/ethyl acetate) to 0.38 g (yield: 96%) of the intended (24E, 24R)-3α,5-cyclo-5α-ergost-22-en-6-one.

m.p. 107° to 109° C. (108° to 110° C. by literature[3]))
IR: 1680 cm$^{-1}$ ($\nu_{c=o}$)
NMR: δ0.73 (3H, s, 18-CH$_3$) 1.01 (3H, s, 19-CH$_3$) 5.1 to 5.3 (2H, m, 22- and 23-H)

[3])Literature: M. J. Thompson et al, Steroids, 7, 745 (1965)

EXAMPLE 13: Synthesis of 24S-ethyl-3α,5-cyclo-5α-cholest-22E-en-6-one 0.41 g (1 mmol) of i-stigmasterol were reacted by the similar manner to Example 12, and the product was purified by means of silica-gel column to 0.38 g (yield: 92.5 %) of the intended ketone.

m.p. 106° to 107° C. (m.p. 102° to 103° C. by literature[2]))
IR: 1675 cm$^{-1}$ ($\nu_{c=o}$)

EXAMPLE 14: Synthesis of (24E, 24R)-3α,5-cyclo-5α-ergost-22-en-6-one 1.37 g (5 mmol) of N-iodophthalimide and 0.37 g (1 mmol) of tetra-n-butylammonium iodide were dissolved in 10 ml of methylene chloride, then a solution of 0.40 g (1 mmol) of i-brassicasterol in 3 ml of methylene chloride was added dropwise thereto. The mixture was reacted and after-treated by a similar manner to Example 12, and purified by means of silicagel column chromatography to give 0.38 g of (24E, 24R)-3α,5-cyclo-5α-ergost-22-en-6-one.

EXAMPLE 15: Synthesis of (22E, 24R)-5α-ergosta-2,22-dien-6-one 484 mg (1.22 mmol) of (22E, 24R)-3α,5-cyclo-5α-ergost-22-en-6-one, 300 mg (1.70 mmol) of pyridinium sulfate and 7 ml of dimethylacetamide were mixed together, and reacted at 160° C. for 5 hours. Then the mixture was cooled to room temperature, and the organic layer was separated by adding ethyl ether and brine. The subsequent washing was repeated and the extract was dried over magnesium sulfate. After distilling off the solvent under reduced pressure, the crude product was purified by a silica-gel column chromatography (hexane/toluene/ethyl acetate =120/2/1) to give 429 mg (88.6 %) of the intended compound, (22E, 24R)-5α-ergosta-2,22-dien-6-one (dienone compound).

m.p. 118° to 120° C. (m.p. 123° to 124° C. by literature[1]))
IR: 1700 cm$^{-1}$ ($\nu_{c=o}$)
$^1$H nmr (CDCl$_3$): δ5.20 (2H, m, 22- and 23-H) 5.61 (2H, m, 2- and 3-H)

1) M. Anastassia, P. Ciuffreds, and A. Fiecchi, J. Chem. Soc., P.T.I. 1983, 379

EXAMPLE 16: Synthesis of (22E, 24R)-5α-ergosta-2,22-dien-6-one 300 mg (0.756 mmol) of (22E, 24R)-3α,5-cyclo-5α-ergost-22-en-6-one, 33 mg (0.166 mmol) of sulfate of triethylamine and 4 ml of sulfolane were mixed together, and subjected to the operations and purification similar to Example 15 to give 256 mg (85.3 %) of the intended dienone compound.

EXAMPLE 17: Synthesis of 24S-ethyl-5α-cholesta-2,22E-dien-6-one 10 ml of toluene were added to 5 ml of triethylamine and 315 mg (1.83 mmol) of p-toluenesulfonic acid, and after reflux in an argon atmosphere for about 15 min., toluene and an excess of triethylamine were distilled off therefrom. Then 500 mg (1.22 mmol) of 24S-ethyl-3α,5-cyclo-5α-cholest-22E-en-6-one and 7 ml of dimethylformamide were added thereto. It was followed by the operations and purification similar to Example 15 to give 403 mg (80.6 %) of the intended dienone compound.

m.p. 114° to 115° C. (m.p. 111° to 112° C. by literature[4])

IR: 1700 cm$^{-1}$ ($\nu_{c=o}$)

$^1$H nmr (CDCl$_3$) δ5.07 (2H, m, 22- and 23-H) 5.58 (2H, m, 2- and 3-H)

4) K. Mori, Agric. Biol. Chem., 44, 1211 (1980)

EXAMPLE 18: Synthesis of 24S-ethyl-5α-cholesta-2,22E-dien-6-one 10 ml of toluene were added to 5 ml of pyridine and 315 mg (1.83 mmol) of p-toluenesulfonic acid, and after reflux for about 15 min, toluene and an excess of pyridine were distilled off therefrom. Then 500 mg (1.22 mmol) of 24S-ethyl-3α,5-cyclo-5α-cholest-22E-en-6-one, 7 ml of toluene and 2 ml of dimethylacetamide were added thereto and heated at 130° C. for 8 hours. It was followed by the operations and purification similar to Example 15 to 418 mg (83.6 %) of the intended dienone compound.

EXAMPLE 19: Synthesis of (22E, 24R)-5α-ergosta-2,22-dien-6-one 300 mg (0.756 mmol) of (22E, 24R)-3α,5-cyclo-5α-ergost-22-en-6-one, 110 mg (1.133 mmol) of sulfamic acid and 4 ml of sulfolane were mixed together, then subjected to the operations an purification similar to Example 15 to give 269 mg (89.7 %) of the intended dienone compound.

EXAMPLE 20: Synthesis of 24S-ethyl-5α-cholesta-2,22E-dien-6-one 550 mg (1.34 mmol) of 24S-ethyl-3α,5-cyclo-5α-cholest-22E-en-6-one, 7 ml of dimethylacetamide and 234 mg (1.35 mmol) of sulfanilic acid were mixed together and heated. Then it was followed by the operations and purification similar to Example 15 to give 484 mg (88.0 %) of the intended dienone compound.

EXAMPLE 21: Synthesis of i-crinosterol ((22E, 24S)-3α,5-cyclo-5α-ergostan-22-en-6β-ol)

i-Crinosterol was prepared in a similar manner as in Example 7. Usual work-up gave the oily intended product (yield: 83 %), its IR and $^1$H NMR spectral data were identical with those of a sample reported by Anastasia et al[5].

5) M. Anastasia, P. Ciuffreda, M. Del Puppo, and A. Fiecchi, J. Chem. Soc. Perkin Trans. 1, 1983, 383

IR: 3060 cm$^{-1}$ ($\nu$hd OH)

$^1$H NMR (CDCl$_3$, ppm): δ3.25 (1H, m, 6-H), 5.1–5.2 (2H, m, 22- and 23-H)

EXAMPLE 22: Synthesis of (22E, 24S)-3α,5-cyclo-5α-ergost-22en-6-one i-Crinosterol was oxidized by Jones reagent in a similar manner as in Example 10, quantitatively.

m.p. 102°–103° C. (lit[1]) 105°–108° C.)

IR: 1670 cm$^{-1}$ ($\nu_{c=o}$)

$^1$H NMR (CDCl$_3$, ppm): δ0.72 (3H, s, 18-CH$_3$), 1.00 (3H, s, 19-CH$_3$), 5.1–5.3 (2H, m, 22- and 23-H)

These physico chemical properties were in agreement with those of the sample reported by Anastasia et al[5].

EXAMPLE 23: Synthesis of (22E, 24S)-5α-ergosta-2,22-dien-6-one

The intended dienone was prepared in a similar manner as Example 15, in 88 % yield.

m.p. 110° to 111° C. (by literature[6] m.p. 111° to 112° C.)

IR: 1700 cm$^{-1}$ ($\nu_{c=o}$)

$^1$H NMR (CDCl$_3$): δ5.2 (2H, m, 22- and 23-H), 5.6 (2H, m, 2-and 3-H)

6) M. Anastasia, P. Allevi, P. Ciuffreda and A. Oleotti, Steroids, 45, 561 (1985)

EXAMPLE 23: Synthesis of (22E, 24R)-5α-ergosta-2,22-diene-6-one 42 ml of toluene and 8.7 ml (62.70 mmol) of triethylamine were added to 5.0 g (12.54 mmol) of brassicasterol and cooled. Under stirring the mixture, 2.0 ml (25.08 mmol) of mesyl chloride were gradually added dropwise thereto. After the reaction was finished, the reaction product was washed by brine, 1N hydrochloric acid and an aqueous sodium bicarbonate respectively in this sequence. Then, 126 ml of acetone, 25 ml of water and 1.29 g (12.17 mmol) of sodium carbonate were added thereto, and reacted by heating under reflux for about 12 hours. After the completion of the reaction was confirmed by means of thinlayer chromatography, acetone was distilled off and the residue was left to cool. The organic layer was separated by adding 58 ml of toluene and brine. The obtained organic layer was cooled and 10 ml of acetone were added thereto. 5.7 ml (CrO$_3$ 1.1 g contained) of Jones reagent were added while kept below 0° C., and further stirred for 2 hours. After the reaction was finished, methanol was added thereto and stirring was continued. After that, the organic layer was separated by adding brine, then washed with an aqueous sodium bicarbonate and by brine, 80 ml of toluene were distilled off. Then 20 ml of dimethylacetamide, 3.9 g (15.5 mmol) of p-toluene sulfonic acid salt of pyridine were added thereto. After refluxing for 8 hours, the reaction mixture was cooled to room temperature, toluene and brine were added thereto to separate the organic layer.

The toluene layer was washed with brine and water, then dried over magnesium sulfate. After distilling off the solvent, the crude product was purified using a silica-gel column chromatography (hexane/toluene/ethyl acetate=120/2/1) to obtain 3.30 g (66.3 %) m.p.: 119° to 119.5° C. (m.p. 123° to 124° C. by literature[1]))

IR: 1700 cm$^{-1}$ ($\nu_{c=o}$)

$^1$H NMR (CDCl$_3$): δ5.20 (2H, m, 22- and 23-H) 5.61 (2H, m, 2- and 3-H)

[1] M. Anastassia, P. Ciuffreds, and Fiecchi J. Chem. Soc., Pakin Trans. I, 1983, 379.

What is claimed is:

1. A process for producing a steroid compound represented by the general formula:

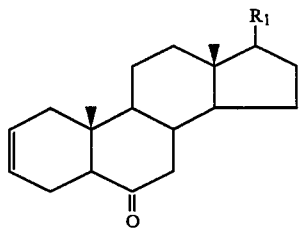

wherein $R_1$ is 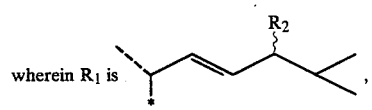, in which $R_2$ is a methyl or ethyl, and * indicates the binding site of $R_1$ to a steroid nucleus,
which comprises reacting a compound represented by the formula:

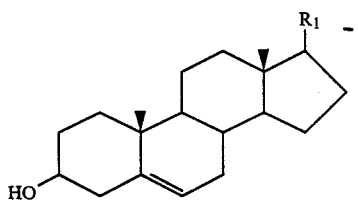

wherein $R_1$ is as defined above, with a compound of the formula: $R_3SO_2X$, wherein $R_3$ is a lower alkyl or a phenyl which may substituted by methyl or chlorine, and X is a chlorine or fluorine atom, in the presence of an organic base in an aromatic or aliphatic hydrocarbon to produce a compound represented by the formula:

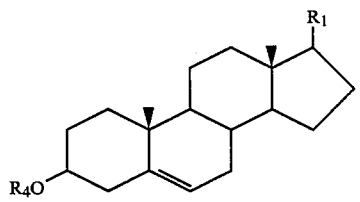

wherein
$R_4$ is $R_3SO_2-$, and
$R_1$ and $R_3$ are as defined above, then reacting the above compound with water in the presence of an inorganic or organic base in a solvent mixture of an aromatic or aliphatic hydrocarbon and an inert and watermiscible organic solvent to produce a compound represented by the formula:

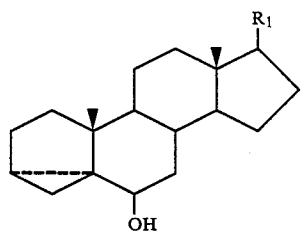

wherein $R_1$ is as defined above,
and subsequently oxidizing the above compound, (1) in the presence of a ketone compound in an aromatic or aliphatic hydrocarbon, or (2) in the presence of a quaternary ammonium halide in an appropriate solvent by means of an N-halocarboxyamide to produce a steroid compound represented by the formula:

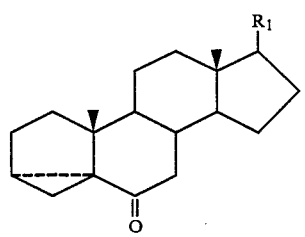

wherein $R_1$ is as defined above, and finally heating the above compound in the presence of an amine salt of an organic or inorganic sulfonic acid or a compound having both sulfo group and amino group in a molecule, in an organic solvent.

2. A process for producing a steroid compound represented by the formula:

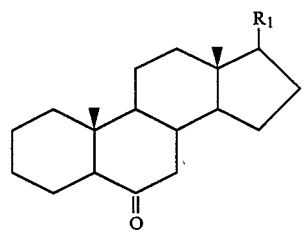

wherein $R_1$ is 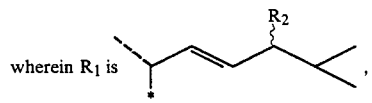, in which $R_2$ is a methyl or ethyl, and * indicates the binding site of $R_1$ to a steroid nucleus, which comprises oxidizing a compound represented by the formula:

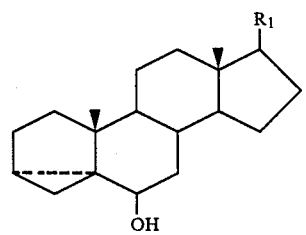

wherein $R_1$ is as defined above,
in the presence of a quaternary ammonium halide in an appropriate solvent by means of an N-halocarboxamide.

3. A process for producing a steroid compound represented by the formula:

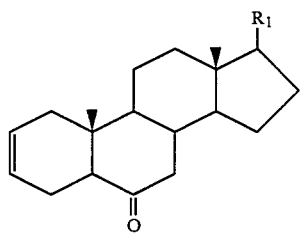 (5)

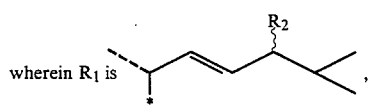

wherein $R_1$ is in which $R_2$ is a methyl or ethyl, and * indicates the binding site of $R_1$ to a steroid nucleus,
which comprises heating a compound represented by the formula:

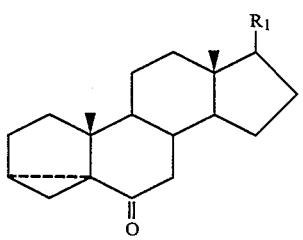 (4)

wherein $R_1$ is as defined above,
in the presence of an amine salt of an organic or inorganic sulfonic acid or a compound having both a sulfo group and an amino group in the same molecule, with an organic solvent.

4. A process for producing a steroid compound represented by the general formula:

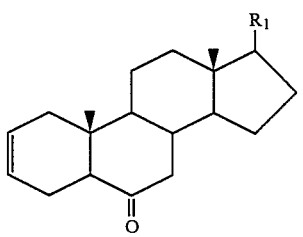 (5)

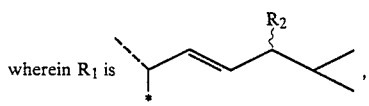

wherein $R_1$ is in which $R_2$ is a methyl or ethyl, and * indicates the binding sit of $R_1$ to a steroid nucleus,
which comprises reacting a compound represented by the formula:

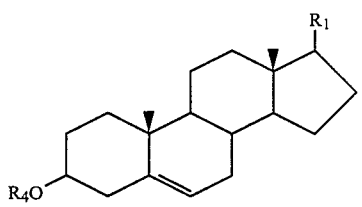 (2)

wherein
$R_4$ is $R_3SO_2$-, and
$R_1$ and $R_3$ are as defined above,
with water in the presence of an inorganic or organic base in a solvent mixture of an aromatic or aliphatic hydrocarbon and an inert and watermiscible organic solvent to produce a compound represented by the formula:

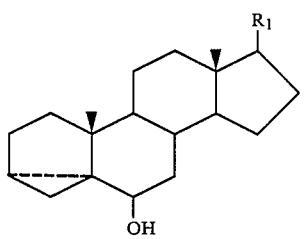 (3)

wherein $R_1$ is as defined above,
and subsequently oxidizing the above compound, (1) in the presence of a ketone compound in an aromatic or aliphatic hydrocarbon, or (2) in the presence of a quaternary ammonium halide in a halogenated hydrocarbon solvent by means of an N-halocarboxyamide to produce a steroid compound represented by the formula:

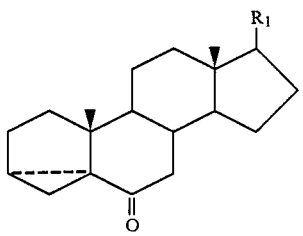 (4)

wherein $R_1$ is as defined above,
and finally heating the above compound in the presence of an amine salt of an organic or inorganic sulfonic acid or a compound having both sulfo group and amino group in a molecule, in an organic solvent.

5. A process for producing a steroid compound represented by the formula:

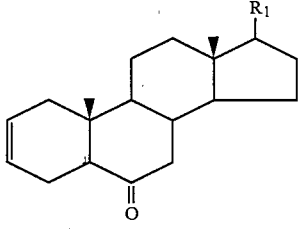 (5)

-continued wherein $R_1$ is 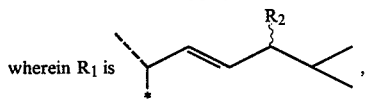, in which $R_2$ is methyl or ethyl, and * indicates the binding side of $R_1$ to a steroid nucleus,
which comprises reacting a compound represented by the formula:

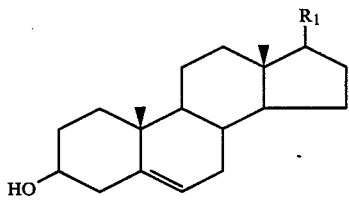 (1)

wherein $R_1$ is as defined above,
with a compound of the formula:

$R_3SO_2X$ wherein $R_3$ is a lower alkyl or a phenyl which may be substituted by methyl or chlorine, and X is a chlorine or fluorine atom,
in the presence of an organic base in an aromatic or aliphatic hydrocarbon to produce a compound represented by the formula:

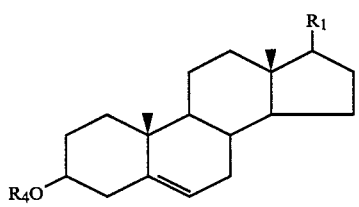 (2)

wherein $R_4$ is $R_3SO_2$-, and $R_1$ and $R_3$ are defined above, then reacting the above compound with water in the presence of an inorganic or organic base in a solvent mixture of an aromatic or aliphatic hydrocarbon and an inert and water-miscible organic solvent to produce a compound represented by the formula:

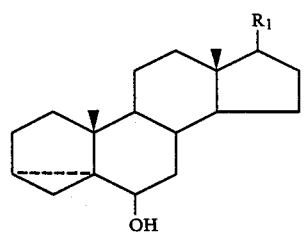 (3)

wherein $R_1$ is as defined above, and subsequently oxidizing the above compound, (1) in the presence of a ketone compound in an aromatic or aliphatic hydrocarbon, or (2) in the presence of a quaternary ammonium halide in an appropriate solvent by means of an N-halocarboxamide, to produce a steroid compound represented by the formula:

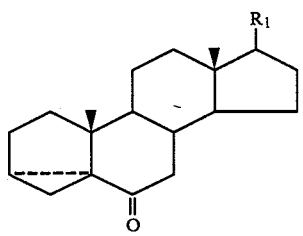 (4)

wherein $R_1$ is as defined above,
and finally heating the above compound in the presence of an amine salt of an organic or inorganic sulfonic acid or a compound having both a sulfo group and an amino group in the same molecule, in a mixture of an aromatic or aliphatic hydrocarbon and an aprotic polar solvent.

6. A process for producing a steroid compound represented by the formula:

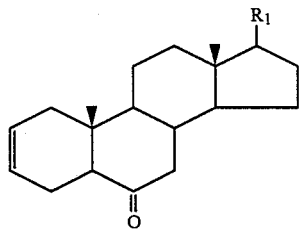 (5)

wherein $R_1$ is 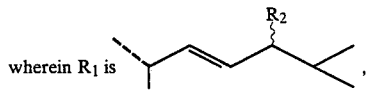, in which $R_2$, is methyl or ethyl, and * indicates the binding site of $R_1$ to a steroid nucleus,
which comprises heating a compound represented by the formula:

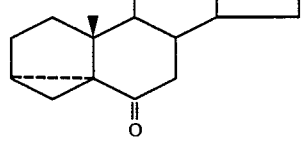 (4)

wherein $R_1$ is as defined above,
in the presence of an amine salt of an organic or inorganic sulfonic acid or a compound having both a sulfo group and an amino group in the same molecule, in a mixture of an aromatic or aliphatic hydrocarbon and an aprotic polar solvent.

7. A process for producing a steroid compound represented by the formula:

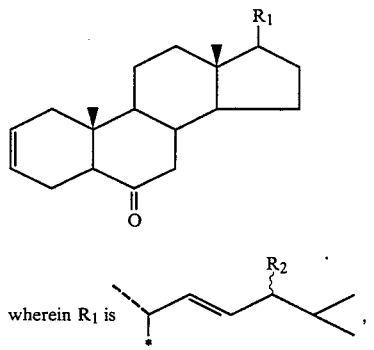

wherein R₁ is 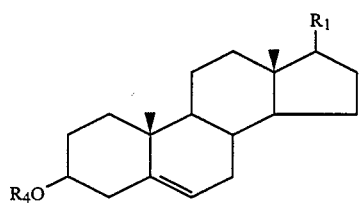, in which R₂ is a methyl or ethyl, and * indicates the binding site of R₁ to a steroid nucleus,
which comprises reacting a compound represented by the formula:

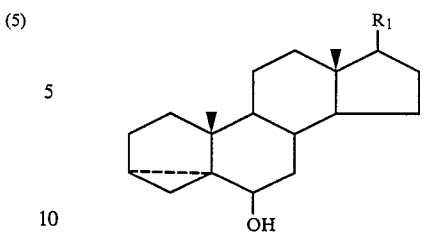

wherein R₁ is as defined above, and subsequently oxidizing the above compound, (1) in the presence of a ketone compound in an aromatic or aliphatic hydrocarbon, or (2) in the presence of a quaternary ammonium halide in an appropriate solvent by means of an N-halocarboxamide to produce a steroid compound represented by the formula:

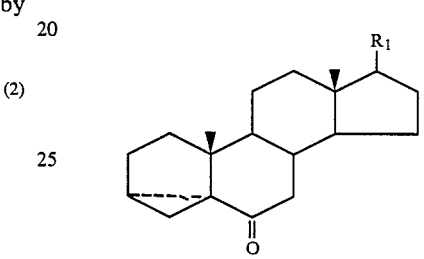

wherein R₄ is R₃SO₂—, and R₁ and R₃ are as defined above,
with water in the presence of an inorganic or organic base in a solvent mixture of an aromatic or aliphatic hydrocarbon and an inert and water-miscible organic solvent to produce a compound represented by the formula:

wherein R₁ is as defined above,
and finally heating the above compound in the presence of an amine salt of an organic or inorganic sulfonic acid or a compound having both a sulfo group and an amino group in the same molecule, in a mixture of an aromatic or aliphatic hydrocarbon and an aprotic polar solvent.

* * * * *